United States Patent [19]

Guillaumet et al.

[11] Patent Number: 5,371,103
[45] Date of Patent: Dec. 6, 1994

[54] THIOCHROMAN COMPOUNDS

[75] Inventors: Gérald Guillaumet; Gérard Coudert, both of Orleans; Tchao Podona, Orleans la Source; Béatrice Guardiola-Lemaitre, Neuilly sur Seine; Pierre Renard, Versailles; Gérard Adam, le Mesnil le Roi; Daniel Henri-Caignard, Paris, all of France

[73] Assignee: Adir et Compagnie, Courbevoie, France

[21] Appl. No.: 133,901

[22] Filed: Oct. 12, 1993

Related U.S. Application Data

[62] Division of Ser. No. 62,424, May 17, 1993, Pat. No. 5,332,741.

[30] Foreign Application Priority Data

May 18, 1992 [FR] France ................... 92 05960

[51] Int. Cl.$^5$ .................. A61K 31/38; C07D 311/04; C07D 335/06
[52] U.S. Cl. ..................... 514/430; 549/23; 546/16; 514/278; 514/432

[58] Field of Search ............. 549/23; 514/430, 432; A61K 31/38

[56] References Cited

U.S. PATENT DOCUMENTS 3,705,167 12/1972 Malen et al. .................. 546/202

Primary Examiner—Cecilia Tsang
Attorney, Agent, or Firm—Gordon W. Hueschen

[57] ABSTRACT

The invention relates to compounds of the formula I:

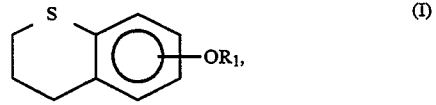

in which $R_1$ is as defined in the description, their optical isomers and their addition salts with a pharmaceutically-acceptable acid or base, and medicinal products which are useful for treating Central Nervous System disorders.

9 Claims, No Drawings

THIOCHROMAN COMPOUNDS

The present application is a division of our prior-filed copending U.S. application Ser. No. 08/062,424, filed May 17, 1993, now U.S. Pat. No. 5,332,741.

The present invention relates to new thiochroman compounds, to a process for the preparation thereof, and to pharmaceutical compositions containing them.

Certain thiochroman compounds of formula (a):

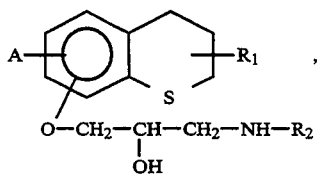

have already been described as antagonists of β-adrenergic receptors (FR 209 20 04) and have proved to be very useful in the treatment of arterial hypertension. Other thiochroman compounds of formula (b):

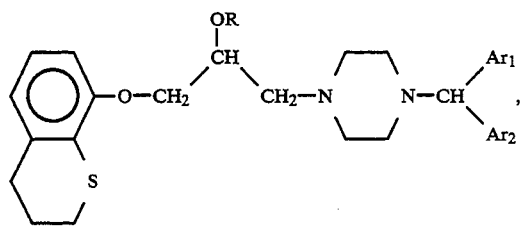

are described in Patent Application EP 458 459 and are claimed for their cardiotonic activity.

Also known is a piperidinoethyloxy-thiochroman compound which likewise has cardiotonic properties and is described in U.S. Pat. No. 3,705,167.

The Applicants have found new thiochroman compounds which surprisingly have a very strong affinity for serotoninergic receptors.

In particular, they have an intense antagonistic activity with regard to 5-HT$_{1A}$ receptors.

Moreover, they prove to have little affinity for β$_1$ and β$_2$ receptors, which is surprising with regard to the prior art.

These characteristics render them useful in therapy, in disorders of the central nervous system (anxiety, depression, stress, psychoses, schizophrenia, pain and disorders of alimentary and sexual functions), without side-effects on the cardiovascular system, since the compounds of the invention have only slight affinity for β receptors, unlike the most similar compounds of the prior art.

The indications of the compounds of the invention therefore differ totally from those—cardiovascular—of the thiochroman compounds of the prior art.

More specifically, the present invention relates to compounds of formula (I):

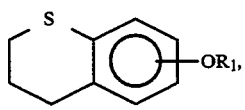

in which:

R$_1$ represents:
a group of formula (A):

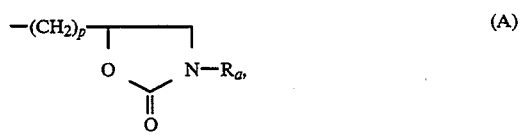

in which R$_a$ represents a hydrogen atom or a lower alkyl radical and p is 1, 2 or 3,
or a group of formula (B):

in which
R$_2$ is a group selected from:
—R'$_2$—, wherein R'$_2$ represents a group —(CH$_2$)$_n$— or

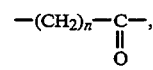

wherein n represents an integer from 1 to 6, R'$_2$ being unsubstituted or substituted in the alkylene moiety by a lower alkyl, aryl or aryl-lower alkyl radical,
—(CH$_2$)$_p$—CH—CH$_2$—,
and

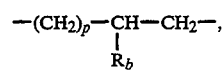

wherein p is 1, 2 or 3 and R$_b$ represents a hydroxy, lower alkoxy, lower alkylcarbonyloxy, aryloxy or aryl-lower alkoxy radical,
R$_3$ and R$_4$, which are identical or different, each independently of the other represents
a hydrogen atom,
a lower alkyl radical that is unsubstituted or substituted by one or more radicals selected from halogen, hydroxy and lower alkoxy,
a cycloalkyl, cycloalkyl-lower alkyl or di(cycloalkyl)-lower alkyl radical each of which is unsubstituted or substituted in the cycloalkyl moieties by one or more radicals selected from halogen, oxo, lower alkyl and lower alkoxy,
a acyl radical that is unsubstituted or substituted by one or more radicals selected from halogen, lower alkyl and lower alkoxy,
a radical selected from adamantyl, benzopyranyl, benzofuryl and aryl, that radical being unsubstituted or substituted by one or more radicals selected from halogen, hydroxy, lower alkyl, lower alkoxy and trifluoromethyl,
an aryl-lower alkyl radical that is unsubstituted or substituted in the aryl nucleus by one or more radicals selected from halogen, hydroxy, lower alkyl, lower alkoxy and trifluoromethyl,
a radical

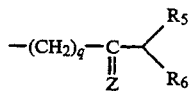

in which q represents 0 or an integer from 1 to 4 and Z represents an oxygen atom or two hydrogen atoms, and in which $R_5$ and $R_6$ each independently of the other represents a hydrogen atom, a lower alkyl radical, a lower acyl radical, an aryl radical that is unsubstituted or substituted by one or more radicals selected from halogen, hydroxy lower alkyl, lower alkoxy and trifluoromethyl; or an aryl-lower alkyl radical that is unsubstituted or substituted in the aryl nucleus by one or more radicals selected from halogen, hydroxy lower alkyl, lower alkoxy and trifluoromethyl, or $R_5$ and $R_6$, together with the nitrogen atom carrying them, form either an unsubstituted or substituted heterocycle selected from pyrrolidine, piperidine, piperazine, morpholine, thiomorpholine, homopiperazine, homopiperidine, phthalimide, and azabicycloalkyl containing from 7 to 12 ring members, or an azaspiroalkyl-lower alkyl group, the azaspiroalkyl system containing from 6 to 12 ring members and being unsubstituted or substituted by one or more radicals selected from halogen, oxo and lower alkyl, with the proviso that when $R_2$ represents a group

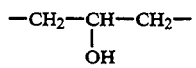

and simultaneously $R_3$ is a hydrogen atom, $R_4$ may not represent a hydrogen atom, a lower alkyl radical or a cycloalkyl radical, or $R_3$ and $R_4$, together with the nitrogen atom carrying them, form:
either an unsubstituted or substituted heterocycle selected from pyrrolidine, piperidine, piperazine, morpholine, thiomorpholine, homopiperazine, homopiperidine, phthalimide, and azabicycloalkyl containing from 7 to 12 ring members,
with the proviso that when $R_2$ represents a group $-(CH_2)_n-$, wherein n is as defined above, $R_3$ and $R_4$ may not form, together with the nitrogen atom carrying them, a piperidino group that is unsubstituted or substituted by one or more lower alkyl or lower alkoxy radicals,
or an azaspiroalkyl group having from 6 to 12 ring members that is unsubstituted or substituted by one or more radicals selected from halogen, oxo, lower alkyl and lower alkoxy,
with the proviso that when $R_2$ represents a group

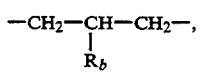

$R_3$ and $R_4$ may not form, together with the nitrogen atom carrying them, a piperazine group substituted at the 4-position by a diphenylmethyl radical that is unsubstituted or substituted in the phenyl nuclei by one or more radicals selected from halogen, lower alkyl, lower alkoxy and trifluoromethyl, wherein, unless indicated otherwise:
the expression "substituted" associated with the term "heterocycle" indicates that the heterocycle is substituted by one or more radicals selected from:
halogen,
hydroxy,
oxo,
lower alkyl,
lower alkoxy,
lower alkoxycarbonyl,
and groups

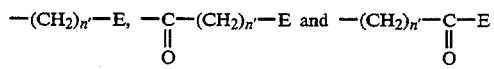

wherein n' represents 0 or an integer from 1 to 4 and E represents a radical selected from aryl, benzhydryl, thienyl, pyrrolyl, pyrrolidinyl, furyl, pyrimidinyl, pyridyl, cycloalkyl and dicycloalkyl-lower alkyl, it being possible for the group E to be unsubstituted or substituted by one or more groups selected from halogen, lower alkyl, lower alkoxy and trifluoromethyl,
the term "cycloalkyl" represents a cyclic group having from 3 to 8 carbon atoms,
the term "acyl" represents a lower alkylcarbonyl, arylcarbonyl or aryl-lower alkylcarbonyl group,
the term "aryl" represents a group selected from phenyl and naphthyl,
and the terms "lower alkyl" and "lower alkoxy" indicate linear or branched groups containing from 1 to 6 carbon atoms, their optical isomers, in pure form or in the form of a mixture, and their addition salts with a pharmaceutically acceptable acid or base.

More especially, $R_3$ and $R_4$, together with the nitrogen atom carrying them, form a piperazine group that is unsubstituted or substituted at the 4-position by a radical selected from:
lower alkyl,
lower alkoxy,
lower alkoxycarbonyl,
and groups

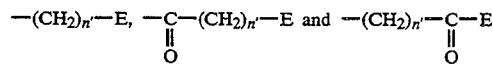

wherein n' represents 0 or an integer from 1 to 4 and E represents a radical selected from aryl, benzhydryl, thienyl, pyrrolyl, pyrrolidinyl, furyl, pyrimidinyl, pyridyl, cycloalkyl and dicycloalkyl-lower alkyl, it being possible for the group E to be unsubstituted or substituted by one or more groups selected from halogen, oxo, hydroxy, lower alkyl, lower alkoxy and trifluoromethyl.

More especially, $R_2$ represents a group $-(CH_2)_n-$ or substituted in their alkylene moiety by a lower alkyl, aryl or aryl-lower alkyl radical.

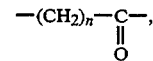

wherein n represents an integer from 1 to 6, it being possible for the groups

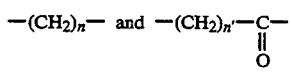

to be

More especially, $R_2$ represents a group

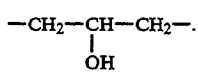

Of the acids used to form the addition salts of the compounds of formula (I) there may be mentioned, by way of non-limiting example, from the mineral series, hydrochloric, hydrobromic, sulphuric and phosphoric acids, and from the organic series, acetic, propionic, maleic, fumaric, tartaric, citric, oxalic, benzoic and methanesulphonic acids.

Of the pharmaceutically acceptable bases that can be used to form an addition salt with the compound of the invention, there may be mentioned, by way of non-limiting exemples, sodium, potassium, calcium and aluminium hydroxide, triethylamine, benzylamine, diethanolamine, tert-butylamine, dicyclohexylamine and arginine.

The invention relates also to a process for the preparation of the compounds of formula (I), characterised in that there is used as starting material a thiochromanol of formula (II):

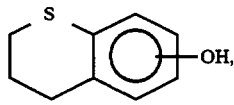

which is reacted:
either with a dihalogenated compound of formula ($II_a$):

$$X_1-R'_2-Y'_1 \qquad (II_a),$$

in which $R'_2$ is as defined in formula (I), $X_1$ represents a halogen atom and $Y'_1$ represents a halogen atom or, when $R'_2$ contains a carbonyl function, a ($C_1$-$C_4$)-alkoxy radical or a hydroxy radical, to give a compound of formula ($II_b$):

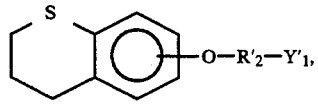

in which $R'_2$ and $Y'_1$ are as defined above, which is reacted, after hydrolysis of the ester function when $Y_1$ represents a ($C_1$-$C_4$)-alkoxy radical, with an amine of formula (IIc):

in which $R_3$ and $R_4$ are as defined in formula (I), to give a compound of formula ($I_1$):

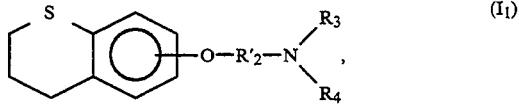

in which $R'_2$, $R_3$ and $R_4$ are as defined above, which is a special case of the compounds of formula (I) wherein $R_1$ represents a group

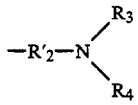

wherein $R'_2$, $R_3$ and $R_4$ are as defined above,
or with a compound of formula ($II_d$) or ($II_{d'}$):

$$X_2-(CH_2)_p-CH=CH_2 \qquad (II_{d'}),$$

wherein $X_2$ represents a halogen atom and p is as defined in formula (I), to give, after treatment with a peracid when a reagent of formula ($II_{d'}$) has been used, a compound of formula ($II_e$):

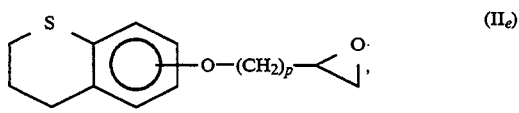

wherein p is as defined above, which compound of formula ($II_e$) is reacted:
either with an amine of formula ($II_c$):

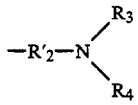

in which $R_3$ and $R_4$ are as defined above, to give a compound of formula ($I_2$):

in which p, $R_3$ and $R_4$ are as defined above, which is a special case of the compounds of formula (I) in which $R_1$ represents a group

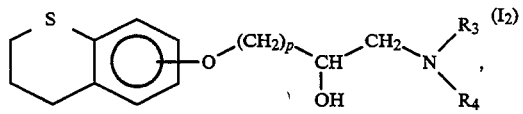

wherein p, $R_3$ and $R_4$ are as defined above, which compounds of formula ($I_2$) are, substituted at the hydroxy group situated in the β-position to the nitrogen atom carrying the radicals $R_3$ and $R_4$, by reaction with a compound of formula ($II_f$):

X₃—R_β    (II_p), in which X₃ represents a halogen atom and R_β is a lower alkyl, lower alkylcarbonyl, aryl or aryl-lower alkyl radical, the terms, "lower alkyl" and "aryl" being as defined in formula (I), the reaction being optionally accompanied by a protection stage of nitrogen carrying R₃ and R₄ to give a product of formula (I₃):

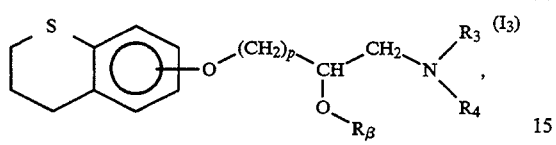

wherein p, R₃, R₄ and R_β are as defined above, which is a special case of the compounds of the general formula (I) wherein R₁ represents a group:

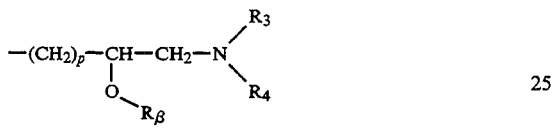

wherein p, R₃, R₄ and R_β are as defined above, or with sodium azide, to give a compound of formula

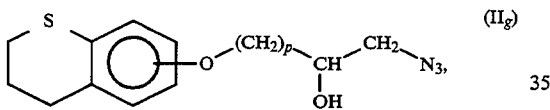

wherein p is as defined above, which is then reacted with ethanol and a Lindlar catalyst in order to obtain a primary amine of formula (I₄):

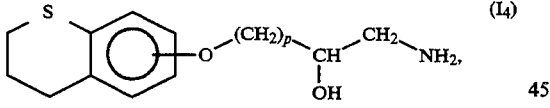

wherein p is as defined above, which is a special case of the compounds of the general formula (I₂) wherein R₁ represents a group:

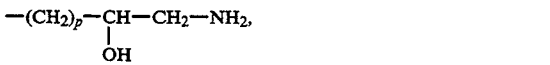

wherein p is as defined above, which compound of formula (I₄) is reacted with N,N'-carbonyl-diimidazole to obtain a compound of formula (I₅):

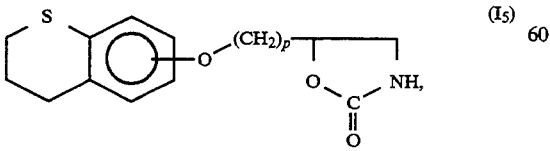

in which p is as defined above, which is a special case of the compounds of formula (I) wherein R₁ represents a group of the formula:

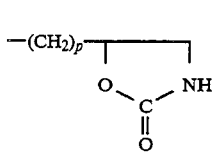

wherein p is as defined above, which compound of formula (I₅) is alkylated, where applicable, by means of a halo-lower alkyl compound of formula (II_h):

R_a'—X₄    (II_h), wherein R_a' is a lower alkyl radical and X₄ is a halogen atom, to give a compound of formula (I₆):

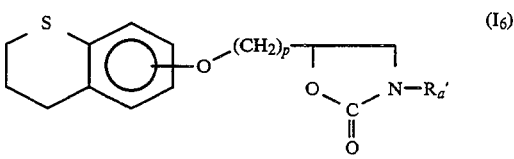

in which p and R_a' are as defined above, which is a special case of the compounds of formula (I) wherein R₁ represents a group of the formula:

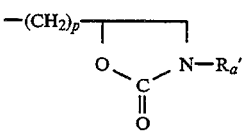

in which p and R_a' are as defined above,
the compounds of formula (I₁), (I₂), (I₃), (I₄), (I₅) and (I₆) forming the compounds of formula (I) in their entirety, which compounds may, if desired, be

- alkylated, if there is a secondary amine, on nitrogen carrying R₃ and R₄ substituents,
- purified by one or more purification methods selected from crystallisation, chromatography over activated a silica column, extraction, filtration, and passage over activated carbon or resin,
- separated, where applicable, in pure form or in the form of a mixture, into their possible optical isomers,
- or converted into a salt with a pharmaceutically acceptable acid or base.

The present invention relates also to a process for the preparation of the compounds of formulae (I₇) and (I₇'):

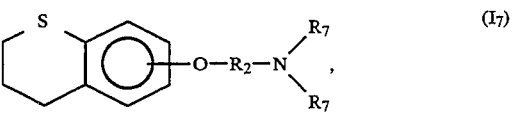

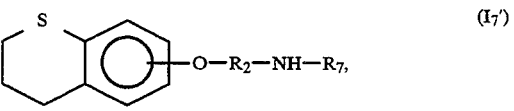

in which R₂ is as defined in formula (I) and R₇ represents:

a lower alkyl radical that is unsubstituted or substituted by one or more radicals selected from halogen, hydroxy and lower alkoxy, a cycloalkyl, cycloalkyl-lower alkyl or di(cycloalkyl)-lower alkyl radical each of which is unsubstituted or substituted, in the cycloalkyl moieties, by one or more radicals selected from halogen, oxo, lower alkyl and lower alkoxy, a acyl radical that is unsubstituted or substituted by one or more radicals selected from halogen, lower alkyl and lower alkoxy, a radical selected from adamantyl, benzopyranyl, benzofuryl, and aryl radical that is unsubstituted or substituted by one or more radicals selected from halogen, lower alkyl, lower alkoxy and trifluoromethyl, an aryl-lower alkyl radical that is unsubstituted or substituted in the aryl nucleus by one or more radicals selected from halogen, lower alkyl, lower alkoxy and trifluoromethyl, or a radical

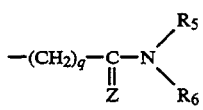

in which q represents 0 or an integer from 1 to 4 and Z represents an oxygen atom or two hydrogen atoms and in which $R_5$ and $R_6$ are as defined in formula (I), the terms "lower alkyl", "lower alkoxy", "cycloalkyl", "acyl" and "aryl" being as defined in formula (I), characterised in that a compound of formula ($I_8$):

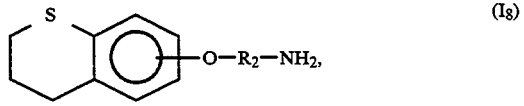

wherein $R_2$ is as defined above, is reacted with a halogenated compound of formula ($II_j$):

$$X_5-R_7 \qquad (II_j),$$

in which $R_7$ is as defined above and $X_5$ represents a halogen atom, to give, depending on the stoichiometry used, a compound of formula ($I_7$) or ($I_7'$) as defined above, which compounds of formulae ($I_7$) and ($I_7'$) may, if desired, be purified by one or more purification methods selected from crystallisation, chromatography over a silica column, extraction, filtration, and passage over activated carbon or resin, separated, where applicable, in pure form or in the form of a mixture, into their possible optical isomers, or converted into a salt with a pharmaceutically acceptable acid or base.

The present invention relates also to a process for the preparation of the compounds of formula ($I_1$):

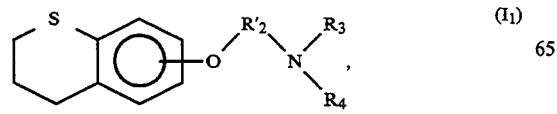

in which $R'_2$, $R_3$ and $R_4$ are as defined in formula (I), which are a special case of the compounds of formula (I) wherein $R_1$ represents a group of the formula:

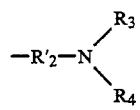

in which $R'_2$, $R_3$ and $R_4$ are as defined above, characterised in that:

a thiochromanol of formula (II):

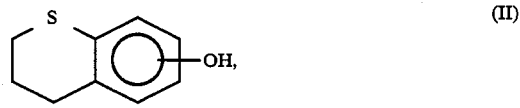

is reacted with a haloalkylamine of formula ($II_j$):

wherein $R'_2$, $R_3$ and $R_4$ are as defined above and $X_6$ represents a halogen atom, to give a compound of formula ($I_1$) as defined above, which compounds of formula ($I_1$) may, if desired, be purified by one or more purification methods selected from crystallisation, chromatography over a silica column, extraction, filtration, and passage over activated carbon or resin, separated, where applicable, in pure form or in the form of a mixture, into their possible optical isomers, or converted into a salt with a pharmaceutically acceptable acid or base.

The present invention relates also to a process for the preparation of the compounds of formula ($I_6$):

wherein p is as defined in formula (I) and $R_a'$ represents a lower alkyl radical,

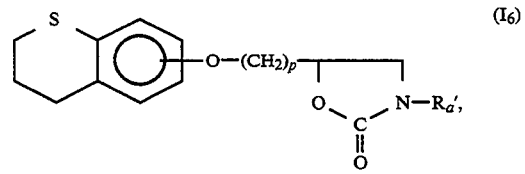

characterised in that a compound of formula ($II_k$):

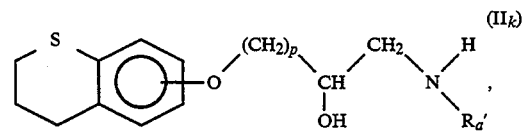

in which p and $R_a'$ are as defined above, which is a special case of the compounds of formula (I) in which $R_1$ represents a group

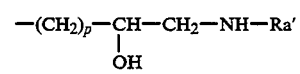

in which $R_a'$ and p are as defined above, is reacted with N,N'-carbonyldiimidazole to obtain a compound of formula ($I_6$) as defined above, which is a special case of the compounds of formula (I) wherein $R_1$ represents a group of the formula:

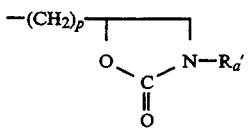

in which $R_a'$ and p are as defined above, which compounds of formula ($I_6$) may, if desired, be
purified by one or more purification methods selected from crystallisation, chromatography over a silica column, extraction, filtration, and passage over activated carbon and/or resin,
separated, where applicable, in pure form or in the form of a mixture, into their optical isomers.

The starting materials used in the processes described above are either included in the literature or readily accessible to the person skilled in the art.

The Applicant has found that the compounds of the invention have very valuable pharmacological properties.

The compounds of the invention surprisingly have a very strong affinity for serotoninergic receptors, and some compounds of the invention have especially an intense antagonistic activity with regard to $5\text{-}HT_{1A}$ receptors.

Binding tests to $5\text{-}HT_{1A}$ receptors have in fact shown that the compounds of the invention behave like very powerful ligands of $5\text{-}HT_{1A}$ serotoninergic receptors.

The antagonistic activity of the compounds of the invention has been demonstrated in vitro and is expressed in vivo by a very strong anxiolytic activity (so-called light/dark cage test in mice, Example F of the present Application), associated with a remarkable antidepressant activity (failed avoidance test in rats, Example E of the present Application).

Accordingly, the compounds of the general formula (I) and their physiologically tolerable salts have valuable pharmacological and therapeutic properties, especially anxiolytic and anti-depressant properties.

Moreover, the compounds of the invention exhibit good selectivity with regard to $5\text{-}HT_{1A}$ receptors, as compared with $\beta_1$ and $\beta_2$ receptors, which is completely surprising in view of the most similar compounds of the state of the art.

That selectivity gives them remarkable pure anxiolytic and anti-depressant properties, without undesirable side-effects on the cardiovascular system.

The compounds of the present invention may therefore be used in the treatment and prevention of stress, anxiety, depression, psychoses, schizophrenia, pain and disorders of alimentary and sexual functions, preferably in the treatment of depression.

Moreover, the compounds of the invention surprisingly potentiate the effects of the known anti-depressants and allow them to take immediate effect (disappearance of the two week latent period generally observed).

The present invention relates also to a pharmaceutical composition containing as active ingredient a compound of the general formula (I) or an addition salt thereof with a pharmaceutically acceptable acid or base, in combination with one or more pharmaceutically acceptable excipients or carriers.

The present invention relates also to a pharmaceutical composition containing as active ingredient at least one compound according to claim 1, or an addition salt thereof with a pharmaceutically acceptable acid or base, in association with at least one known anti-depressant active ingredient, in combination with one or more pharmaceutically acceptable excipients or carriers.

Of the pharmaceutical compositions according to the invention there may be mentioned, by way of non-limiting example, those which are suitable for oral, rectal, nasal or parenteral administration, and especially tablets, dragées, soft gelatin capsules, paquets, sachets, granules, pills, granulates, suppositories, creams, ointments, aerosols, capsules, dermic gels, and injectable or drinkable solutions.

The dosage varies from one individual to another, depending on the age, weight and sex of the patient, the chosen mode of administration, and the nature and severity of the disorder. The doses used range from 0.1 to 100 mg per treatment (in particular 0,1 to 10 mg, for example 1 to 10 mg), divisible into from 1 to 3 doses per 24 hour period.

The following Examples illustrate the invention and do not limit it in any way.

EXAMPLE 1

8-{{3-[4-(2-Methoxyphenyl)piperazin-1-yl]-2-hydroxypropyl}oxy}thiochroman

Step A: 8-(2,3-Epoxypropoxy)thiochroman 5 g (30.08 mmol) of 8-thiochromanol are dissolved under argon in 30 cm³ of N,N-dimethylformamide. 800 mg (33.09 mmol) of sodium hydride are added and the mixture is brought to 60° C., with stirring.

After 15 minutes, 18.8 cm³ (240.61 mmol) of epichlorohydrin are added. The mixture is left for one hour at 60° C.

The N,N-dimethylformamide is evaporated off. The residue is slowly taken up in water and extracted with methylene chloride. The product is purified over a silica column, yielding 8-(2,3-epoxypropoxy)thiochroman (eluant: pure methylene chloride).

8-(2,3-epoxypropoxy)thiochroman is recovered in the form of a colourless oil.

Yield: 65%

Step B: 8-{{3-[4-(2-Methoxyphenyl)piperazin-1-yl]-2-hydroxypropyl}oxy}thiochroman 140 mg (0.63 mmol) of the compound obtained in Step A are dissolved in 1.5 cm³ of anhydrous tetrahydrofuran. 600 mg (3.15 mmol) of 1-(2-methoxyphenyl)-piperazine, diluted in 1.5 cm³ of anhydrous tetrahydrofuran, are added.

The mixture is refluxed, under argon and with stirring, for 15 hours. The tetrahydrofuran is evaporated off, and the residue is taken up in water, extracted with methylene chloride and dried over magnesium sulphate.

The product is purified over a silica column (eluant: methanol/methylene chloride 5:95).

There are recovered 255 mg of 8-{{3-[4-(2-methoxyphenyl) piperazin-1-yl]-2-hydroxypropyl}oxy}thiochroman, which is washed with ether.

Yield: 98% Melting point: 134°-135° C. Nuclear magnetic resonance (CDCl₃+D₂O) CH₂—CH₂—S: 2.01 to 2.11 ppm (2H, m) CH₂—N: 2.69 to 2.72 ppm (4H, m)

CH$_2$—N; CH$_2$—aromatic: 2.83 to 2.92 ppm (4H, m) CH$_2$—S (J=5.8 Hz): 3.00 ppm (2H, t) CH$_2$—N—aromatic: 3.13 to 3.17 ppm (4H, m) CH$_3$—O: 3.87 ppm (3H, s) CH$_2$—O: 4.09 ppm (2H, m) CH—OH: 4.19 ppm (1H, m) aromatic (J=7.9 Hz): 6.72 ppm (2H, d) aromatic: 6.84 to 7.06 ppm (5H, m)

EXAMPLE 2

8-{{4-[4-(2-Methoxyphenyl)piperazin-1-yl]butyl}oxy} thiochroman

Step A: 8-[(4-Bromobutyl)oxy]thiochroman 300 mg of 8-thiochromanol are dissolved in 3 cm$^3$ of N,N-dimethylformamide, under argon. 430 mg (1.985 mmol) of 1,4-dibromobutane diluted in 3 cm$^3$ of N,N-dimethylformamide are added.

Then 750 mg of potassium carbonate are added using a spatula.

The mixture is heated at 65° C., under argon and with stirring, for 3 hours 30 minutes.

The N,N-dimethylformamide is evaporated off. The residue is taken up in water and extracted with methylene chloride, before being purified over a silica column (eluant: ether/petroleum ether 15:85).

240 mg of white crystals of 8-[(4-bromobutyl)oxy]thiochroman are recovered.

Step B: 8-{{4-[4-(2-Methoxyphenyl)piperazin-1-yl]butyl}oxy} thiochroman 1.5 g (4.98 mmol) of the compound obtained in Step A are dissolved in 15 cm$^3$ of acetonitrile, under argon. 0.94 g (7.47 mmol) of N,N-diisopropylethylamine diluted in 11 cm$^3$ of acetonitrile is added, followed by 1.44 g (0.747 mmol) of 1-(2-methoxyphenyl)piperazine dissolved in 11 cm$^3$ of acetonitrile.

The mixture is refluxed for 15 hours, then the acetonitrile is evaporated off, and the residue is taken up in water, extracted with methylene chloride and dried over magnesium sulphate, before being purified over a silica column (eluant: methanol/methylene chloride 5:95).

1.98 g of 8-{{4-[4-(2-methoxyphenyl)piperazin-1-yl]butyl}oxy}thiochroman are recovered.

Yield: 97% Melting point: 61° C. Nuclear magnetic resonance (CDCl$_3$+D$_2$O): CH$_2$—CH$_2$—N: 1.75 to 1.77 ppm (2H, m) CH$_2$—CH$_2$—O: 1.87 to 1.89 ppm (2H, m) CH$_2$—CH$_2$—S: 2.00 to 2.10 ppm (2H, m) CH$_2$—N (J=7.2 Hz): 2.50 ppm (2H, t) CH$_2$—N (J=5.5 Hz): 2.68 ppm (4H, t) CH$_2$—Ar (J=6.2 Hz): 2.83 ppm (2H, t) CH$_2$—S (J=5.8 Hz): 3.00 ppm (2H, t) CH$_2$—N—Ar (J=5.5 Hz): 3.10 ppm (4H, t) CH$_3$—O: 3.89 ppm (3H, s) CH$_2$—O (J=6.3 Hz): 4.03 ppm (2H, t) aromatic: 6.65 to 7.05 ppm (7H, m)

EXAMPLE 3

8-{{4-[4-(3-Trifluoromethylphenyl)piperazin-1-yl]butyl}oxy}thiochroman

Following the procedure of Example 2 but replacing 1-(2-methoxyphenyl)piperazine in Step B with 1-(3-trifluoromethylphenyl)piperazine, the title compound is obtained.

Yield: 90% Melting point (oxalate): 105° C. Nuclear magnetic resonance (CDCl$_3$+D$_2$O): CH$_2$—CH$_2$—O,CH$_2$—CH$_2$—N: 1.72 to 1.90 ppm (4H, m) CH$_2$—CH$_2$—S: 2.00 to 2.10 ppm (2H, m) CH$_2$—N (J=7 Hz): 2.50 (2H, t) CH$_2$—N (J=5.5 Hz): 2.65 (4H, t) CH$_2$—Ar (J=6.2 Hz): 2.81 (2H, t) CH$_2$—S (J=5.8 Hz): 3.00 (2H, t) CH$_2$—N—Ar (J=5.5 Hz): 3.24 (4H, t) CH$_2$—O (J=6.3 Hz): 4.05 (2H, t) aromatic (J=7.9 Hz): 6.65 ppm (2H, t) aromatic (J=7.9 Hz): 6.93 ppm (1H, t) aromatic: 7 to 7.12 ppm (3H, m) aromatic (J=8.3 Hz): 7.32 ppm (1H, t)

EXAMPLES 4 AND 5

Following the procedure of Examples 2 and 3 but replacing 8-thiochromanol by 7-thiochromanol, the following compounds are obtained:

EXAMPLE 4

7-{{4-[4-(2-Methoxyphenyl)piperazin-1-yl]butyl}oxy} thiochroman

EXAMPLE 5

7-{{4-[4-(3-Trifluoromethylphenyl)piperazin-1-yl]butyl}oxy}thiochroman

EXAMPLE 6

8-{[4-Bis(4-fluorophenyl)methylpiperazin-1-yl]butyloxy}thiochroman

Following the procedure of Example 2 but replacing 1-(2-methoxyphenyl)piperazine in Step B with 1-bis(4-flucrophenyl)methylpiperazine, the title compound is obtained.

Yield: 96% Melting point (oxalate): 194° C. Nuclear magnetic resonance (CDCl$_3$): CH$_2$—CH$_2$—N: 1.69 to 1.72 ppm (2H, m) CH$_2$—CH$_2$—O: 1.80 to 1.84 ppm (2H, m) CH$_2$—CH$_2$—S: 2.00 to 2.10 ppm (2H, m) CH$_2$—N: 2.29 to 2.58 ppm (10H, m) CH$_2$—aromatic (J=6.2 Hz): 2.81 ppm (2H, t) CH$_2$—S (J=5.8 Hz): 2.98 ppm (2H, t) CH$_2$—O (J=6.3 Hz): 4.00 ppm (2H, t) CH—aromatic: 4.21 ppm (1H, s) aromatic (J=7.9 Hz) 6.64 ppm (2H, t) aromatic (J=7.9 Hz): 6.91 ppm (1H, t) aromatic (J=8.3 Hz): 6.96 ppm (4H, t) aromatic (J=8.3 Hz) 7.34 and 7.36 ppm (4H, 2d)

EXAMPLE 7

8-{[3-(Morpholin-4-yl)-2-hydroxypropyl]oxy}thiochroman

Following the procedure of Example 1 but replacing 1-(2-methoxyphenyl)piperazine in Step B with morpholine, the title compound is obtained.

EXAMPLE 8

8-[6-Perhydroazepinylhexyloxy]thiochroman

Following the procedure of Example 1 but replacing 1-(2-methoxyphenyl)piperazine in Step B with perhydroazepine, the title compound is obtained.

EXAMPLE 9

8-{[4-(7,9-Dioxo-8-azaspiro[4.5]decan-8-yl)-butyl]oxy} thiochroman 2 g (6.62 mmol) of 8-(4-bromobutyl)-8-azaspiro[4.5]-decane-7,9-dione, 2.5 g (18.04 mmol) of potassium carbonate and a catalytic amount of potassium iodide are added, with stirring, to 1 g (6.015 mmol) of 8-thiochromanol dissolved in 10 cm$^3$ of N,N-dimethylformamide.

The mixture is heated at 60° C., with stirring, for 20 hours and then cooled, and the solvent is evaporated off under reduced pressure. The residue is taken up in 10 cm$^3$ of water and the product is extracted with methylene chloride.

Drying over magnesium sulphate and evaporating off the solvent yield 2.29 g of 8-[(4-(7,9-dioxo-8-azaspiro[4.5]decan-8-yl)butyl)oxy]thiochroman, after purification by chromatography over a silica column (eluant: diethyl ether/petroleum ether 1:1).

Yield: 98% Melting point: 69° C. Nuclear magnetic resonance (CDCl₃+D₂O): CH₂: 1.44 to 1.83 ppm (12H, m) CH₂—CH₂—S: 2.00 to 2.10 ppm (2H, m)

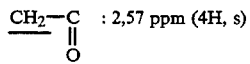 : 2,57 ppm (4H, s)

CH₂—aromatic (J=6.3 Hz): 2.77 ppm (2H, t) CH₂—S (J=5.8 Hz): 2.95 ppm (2H, t) CH₂—N—CO (J=7 Hz): 3.82 ppm (2H, t) CH₂—O (J=6.3 Hz): 3.98 ppm (2H, t) aromatic (J=7.9 Hz): 6.62 ppm (2H, t) aromatic (J=7.9 Hz): 6.89 ppm (1H, t)

EXAMPLES 10 TO 22

Following the procedure of Example 9 but replacing 8-(4-bromobutyl)-8-azaspiro[4.5]decane-7,9-dione by the appropriate halogenated compounds, the following are obtained in the same manner:

EXAMPLE 10
8-{[4-(4-Hydroxypiperidin-1-yl)butyl]oxy}thiochroman

EXAMPLE 11
8-{{4-[4-(Ethoxycarbonyl)piperidin-1-yl]butyl}oxy}thiochroman

EXAMPLE 12
8-{[2-(Diethylamino)ethyl]oxy}thiochroman

EXAMPLE 13
8-{[(Tert.-butylamino)ethyl]oxy}thiochroman

EXAMPLE 14
8-{[3-(Cyclohexylamino)propyl]oxy}thiochroman

EXAMPLE 15
8-{[4-(N-ethyl-N-cyclopentylamino)butyl]oxy}thiochroman

EXAMPLE 16
8-{[2-(7,9-Dioxo-8-azaspiro[4.5]decan-8-yl)ethyl]oxy}thiochroman

EXAMPLE 17
8-{{2-{[4-(7,9-Dioxo-8-azaspiro[4.5]decan-8-yl)butyl]amino}ethyl}oxy}thiochroman

EXAMPLE 18
8-{{3-[4-(2-Methoxyphenyl)piperazin-1-yl]propyl}oxy}thiochroman

EXAMPLE 19
8-{[4-(1-Azaspiro[5.5]undecan-1-yl)butyl]oxy}thiochroman

EXAMPLE 20
8-{{2-{4-[2-(Methoxy)phenyl]piperidin-1-yl}ethyl}oxy}thiochroman

EXAMPLE 21
8-{{2-{[2-(Phthalimido)ethyl]amino}ethyl}oxy}thiochroman

EXAMPLE 22
8-{{2-{[2-(Phthalimidocarbonyl)ethyl]amino}ethyl}oxy}thiochroman

EXAMPLE 23
8-{[3-(3-Methylcyclohexylamino)-2-hydroxypropyl]oxy}thiochroman

Following the procedure of Example 1 but replacing 1-(2-methoxyphenyl)piperazine in Step B with 3-methylcyclohexylamine, the title compound is obtained.

EXAMPLE 24
8-{{3-[4-(Pyrimidin-2-yl)piperazin-1-yl]-2-hydroxypropyl}oxy}thiochroman Following the procedure of Example 1 but replacing 1-(2-methoxyphenyl)piperazine in Step B with 1-(pyrimidin-2-yl)piperazine, the title compound is obtained.

Yield: 88% Melting point (oxalate): 200° C. Nuclear magnetic resonance (CDCl₃+D₂O): CH₂—CH₂—S: 2.00 to 2.10 ppm (2H, m) CH₂—N: 2.50 to 2.77 ppm (6H, m) CH₂—aromatic (J=6.3 Hz): 2.81 ppm (2H, t) CH₂—S (J=5.8 Hz): 3.00 ppm (2H, t) CH₂—N (J=6.2

Hz): 3.88 ppm (4H, t) CH$_2$—O (J=6.5 Hz): 4.08 ppm (2H, d) CH—OH: 4.16 to 4.20 ppm (1H, m) aromatic (J=5 Hz): 6.50 ppm (1H, t) aromatic (J=7.9 Hz): 6.71 ppm (2H, d) aromatic (J=7.9 Hz): 6.95 ppm (1H, t) aromatic (J=5 Hz): 8.31 ppm (2H, d)

EXAMPLE 25

8-{{3-[4-(3-Trifluoromethylphenyl)piperazin-1-yl]-2-hydroxypropyl}oxy}thiochroman Following the procedure of Example 1 but replacing 1-(2-methoxyphenyl)piperazine in Step B with 1-(3-trifluoromethylphenyl)piperazine, the title compound is obtained.

Yield: 90% Melting point (oxalate): 226° C. Nuclear magnetic resonance (CDCl$_3$+D$_2$O): CH$_2$—CH$_2$—S: 2.00 to 2.10 ppm (2H, m) CH$_2$—N: 2.67 to 2.70 ppm (4H, m) CH$_2$—aromatic, CH$_2$—N: 2.81 to 2.84 ppm (4H, m) CH$_2$—S (J=5.9 Hz): 3.00 ppm (2H, t) CH$_2$—N-aromatic (J=5.1 Hz): 3.27 ppm (4H, t) CH$_2$—O: 4.04 to 4.06 ppm (2H, m) CH—OH: 4.17 ppm (1H, m) aromatic (J=7.9 Hz): 6.69 ppm (2H, d) aromatic (J=7.9 Hz): 6.94 ppm (1H, t) aromatic: 7.06 to 7.08 ppm (3H, m) aromatic (J=7.9 Hz): 7.35 ppm (1H, t)

EXAMPLES 26 AND 27

Following the procedure of Example 1 but replacing 1-(2-methoxyphenyl)piperazine in Step B with the appropriate amines, the following compounds are obtained:

EXAMPLE 26

8-{[3-(4-Benzylpiperazin-1-yl)-2-hydroxypropyl]oxy}thiochroman

EXAMPLE 27

8-{{3-{4-[2-(2-Methylphenyl)ethyl]piperazin-1-yl}-2-hydroxypropyl}oxy}thiochroman

EXAMPLE 28

8-{[3-(7,9-Dioxo-8-azaspiro[4.5]decan-8-yl)-2-hydroxypropyl]oxy}thiochroman

Following the procedure of Example 1 but replacing 1-(2-methoxyphenyl)piperazine in Step B with 8-azaspiro[4.5]decane-7,9-dione, the title compound is obtained (oil).

Nuclear magnetic resonance (CDCl$_3$+D$_2$O): CH$_2$: 1.51 to 1.55 ppm (4H, m) CH$_2$: 1.68 to 1.72 ppm (4H, m) CH$_2$—CH$_2$—S: 2.00 to 2.12 ppm (2H, m) CH$_2$—CO: 2.65 ppm (4H, s) CH$_2$—aromatic (J=6.2 Hz): 2.81 ppm (2H, t) CH$_2$—S (J=5.8 Hz): 3.00 ppm (2H, t) CH$_2$—N—CO, CH—O—aromatic: 3.96 to 4.10 ppm (3H, m) CH—OH: 4.13 to 4.17 ppm (1H, m) CH—O—aromatic (J=8.5 Hz): 4.29 ppm (1H, dd) aromatic (J=7.9 Hz): 6.65 and 6.69 ppm (2H, 2d) aromatic (J=7.9 Hz): 6.92 ppm (1H, t)

EXAMPLE 29

8-{[3-(4-Azaspiro[5.5]undecan-4-yl)-2-hydroxypropyl]oxy}thiochroman

Following the procedure of Example 1 but replacing 1-(2-methoxyphenyl)piperazine in Step B with 1-azaspiro[5.5]undecane, the title compound is obtained.

EXAMPLES 30 TO 32

Following the procedure of Examples 1, 25 and 28 but replacing 8-thiochromanol with 6-thiochromanol, the following compounds are obtained:

EXAMPLE 30

6-{{3-[4-(2-Methoxyphenyl)piperazin-1-yl]-2-hydroxypropyl}oxy}thiochroman

EXAMPLE 31

6-{{3-[4-(3-Trifluoromethylphenyl)piperazin-1-yl]-2-hydroxypropyl}oxy}thiochroman

EXAMPLE 32

6-{[3-(7,9-Dioxo-8-azaspiro[4.5]decan-8-yl)-2-hydroxypropyl]oxy}thiochroman

EXAMPLE 33

8-{[5-(7,9-Dioxo-8-azaspiro[4.5]decan-8-yl)-4-hydroxypentyl]oxy}thiochroman

EXAMPLE 34

8-{{3-{N,N-di-[4-(7,9-dioxo-8-azaspiro[4.5]decan-8-yl)-but-1-yl]amino}-2-hydroxypropyl}oxy}thiochroman Step A: 8-(2,3-Epoxypropoxy)thiochroman The procedure of Step A of Example 1 is followed, starting from 1.72 g (10.34 mmol) of thiochromanol and 7.653 g (82.72 mmol) of epichlorohydrin. 1.5 g (6,721 mmol) of 2,3-epoxypropoxythiochroman are obtained.

Yield: 65%

Step B:
8-[(3-Amino-2-hydroxypropyl)oxy]thiochroman 1.494 g (6.72 mmol) of the compound obtained in Step A, dissolved in a dioxane/water mixture, are reacted with 0.612 g (9.41 mmol) of sodium azide. The mixture is heated under reflux for 8 hours and then cooled, and the solvent is evaporated off under reduced pressure.

The crude product is taken up in water and then extracted with methylene chloride.

The organic phase is dried over magnesium sulphate and then evaporated, yielding, after purification over a silica column (eluant: petroleum ether/diethylether), 1.23 g of 2-hydroxy-3-[(thiochroman-8-yl)oxy]propane nitride (yield: 69%) which is placed, in the presence of ethanol and of Lindlar catalyst, in a hydrogenator at 25° C. for 8 hours, to give 8-[(3-amino,-2-hydroxypropyl)oxy]thiochroman.

Yield: 97%

Step C:
8-{{3-[N,N-di-(4-(7,9-dioxo-8-azaspiro[4.5]decan-8-yl)-but-1-yl)amino]-2-hydroxypropyl}oxy}thiochroman 1.36 g (4.498 mmol) of 8-(4-bromobutyl)-8-azaspiro[4.5]decane-7,9-dione are dissolved in 11 cm$^3$ of acetonitrile, under argon. 1.077 g (4.498 mmol) of the compound obtained in Step B are added, followed by 1.21 g of diisopropylethylamine diluted in 14.5 cm$^3$ of acetonitrile.

The mixture is refluxed, under argon and with stirring, for 15 hours.

The acetonitrile is evaporated off, and the residue is taken up in water before being extracted with methylene chloride. After drying over magnesium sulphate, the resulting 8-{(3-[N,N-di-(4-(7,9-dioxo-8-azaspiro[4.5]decan-8-yl)-but-1-yl)amino]-2-hydroxypropyl)oxy}thiochroman is purified over a silica column (eluant: methanol/methylene chloride 5:95).

Melting point (oxalate): 72°–73° C.

EXAMPLE 35

8-{{3-[N,N-di-(2-phenylethyl)amino]-2-hydroxypropyl}oxy}thiochroman

Following the procedure of Example 34 but replacing 8-(4-bromobutyl)-8-azaspiro[4.5]decane-7,9-dione in Step C with 1-bromo-2-phenylethyl, the title compound is obtained.

EXAMPLE 36

8-{{[3-(N-tert.-butyl-N-benzylamino)-2-hydroxy]-propyl}oxy}thiochroman

Following the procedure of Example 1 but replacing 1-(2-methoxyphenyl)piperazine in Step B with N-tert.-butylbenzylamine, the title compound is obtained.

EXAMPLE 37

8-{{3-[N-sec.-butyl-N-(2,6-dihydroxybenzyl)amino]-2-hydroxy)propyl]oxy}thiochroman Following the procedure of Example 1 but replacing 1-(2-methoxyphenyl)piperazine in Step B with N-sec.-butyl-2,6-dihydroxybenzylamine, the title compound is obtained.

EXAMPLE 38

8-{{3-[4-(2-Methoxyphenyl)piperazin-1-yl]-2-methoxypropyl}oxy}thiochroman 100 mg (2.41×10$^{-4}$ mol) of the compound of Example 1 are dissolved, under argon and with stirring, in 2 cm$^3$ of anhydrous tetrahydrofuran.

9 mg (3.62×10$^{-4}$ mol) of sodium hydride are added in small portions. Then 171 mg (1.20 mmol) of methyliodide are added dropwise.

The mixture is left at room temperature for 30 minutes. The solvent is evaporated off, and then the residue is taken up in water. The mixture is extracted with methylene chloride. The product is dried over magnesium sulphate.

Purification is carried out over a silica column (eluant: ether/petroleum ether 1:1, then ether: 100%).

90 mg of 8-{{3-[4-(2-methoxyphenyl)piperazin-1-yl]-2-methoxypropyl}oxy}thiochroman are recovered.

Yield: 87% Melting point: 123° C.

EXAMPLE 39

8-[(3-TERT.-butylamino-2-methoxyprop-1-yl)oxy]thiochroman

Following the procedure of Example 1 but replacing 1-(2-methoxyphenyl)piperazine in Step B with N-tert.-butylamine, then proceeding, with the resulting compound, as in Example 38, the title compound is obtained.

Yield: 83% Melting point (oxalate): 185° C. Nuclear magnetic resonance (CDCl$_3$): CH$_3$—C: 1.13 ppm (9H, s) NH: 1.66 ppm (1H, unresolved peak) CH$_2$—CH$_2$—S: 2.00 to 2.10 ppm (2H, m) CH$_2$—aromatic, CH$_2$—N: 2.78 to 2.82 ppm (4H, m) CH$_2$—S (J=5.8 Hz): 3.00 ppm (2H, t) CH$_3$—O: 3.54 ppm (3H, s) CH—O: 3.71 to 3.75 ppm (1H, m) CH$_2$—O: 4.06 to 4.10 ppm (2H, m) aromatic (J=7.9 Hz): 6.66 ppm (2H, d) aromatic (J=7.9 Hz): 6.94 ppm (1H, t)

EXAMPLE 40

8-{{3-[4-(3-Trifluoromethylphenyl)piperazin-1-yl]-2-methoxypropyl}oxy}thiochroman Following the procedure of Example 38 but starting from the compound of Example 25, the title compound is obtained.

EXAMPLE 41

8-{{3-[4-(2-Methoxyphenyl)piperazin-1-yl]-2-(acetyloxy)propyl}oxy}thiochroman Analogously to Example 38, but using acetyl chloride in place of methyliodide, 8-{{3-[4-(2-methoxyphenyl)-piperazin-1-yl]-2-(acetyloxy)propyl}oxy}thiochroman is obtained.

EXAMPLE 42

8-{[3-(7,9-Dioxo-8-azaspiro[4.5]decan-8-yl)propyl]oxy}thiochroman

Following the procedure of Example 2 but replacing 1,4-dibromobutane in Step A with 1,3-dibromopropane and replacing 1-(2-methoxyphenyl)piperazine in Step B with the appropriate amine, the title compound is obtained.

Melting point: below 50° C.

EXAMPLE 43

8-{{3-[4-(2-Methoxyphenyl)piperazin-1-yl]-propyl}oxy}thiochroman

Following the procedure of Example 2 but replacing 1,4-dibromobutane in Step A with 1,3-dibromopropane, the title compound is obtained.

Melting point (oxalate): 115° C.

EXAMPLE 44

8-{{2-[4-(2-Methoxyphenyl)piperazin-1-yl]-ethyl}oxy}thiochroman

Step A: 8-[(2-Bromoethyl)oxy]thiochroman 1 g (6.015 mmol) of 8-thiochromanol is dissolved in 2.26 g (12.03 mmol) of 1,2-dibromoethane. 5.6 cm$^3$ of a 1.6N NaOH solution are added dropwise. The mixture is heated to 100° C.; after 2 hours, the solution reaches pH 7. The mixture is allowed to cool. 100 cm$^3$ of a 2N NaOH solution are added. The mixture is extracted with CH$_2$Cl$_2$ and then dried over MgSO$_4$. Purification over a silica column (eluant: petroleum ether/CH$_2$Cl$_2$ 2:1) yields the desired compound.

Yield: 32% Melting point: 64° C.

Step B: 8-{{2-[4-(2-Methoxyphenyl)piperazin-1-yl]-ethyl}oxy}thiochroman

Under argon and with stirring, 710 mg (2.6 mmol) of brominated compound are dissolved in 5 cm$^3$ of CH$_3$CN. N,N-diisopropylethylamine dissolved in 6 cm$^3$ of CH$_3$CN is added, followed by 1-(2-methoxyphenyl)-piperazine dissolved in 6 cm$^3$ of CH$_3$CN. The mixture is refluxed for one night. The solvent is evaporated off. The residue is taken up in H$_2$O and then extracted with CH$_2$Cl$_2$ and dried over MgSO$_4$. The product is purified over a silica column (eluant:ether).

Yield: 75% Melting point: 79° C.

EXAMPLE 45

8-{[(2-Oxo-3-TERT.-butyloxazolidin-5-yl)methyl]oxy}thiochroman 1.63 g (10.08 mmol) of N,N'-carbonyldiimidazole are added to 0.2 g (0.677 mmol) of 8-{[3-(tert.-butylamino)-2-hydroxypropyl]oxy}thiochroman dissolved in 10 cm$^3$ of anhydrous tetrahydrofuran.

The mixture is heated under reflux, with stirring, for 2 hours and then cooled, and the solvent is evaporated off under reduced pressure.

The crude product is then purified by chromatography over a silica column (solvent: methylene chloride). 0.21 g of 8-{[(2-oxo-3-tert.-butyloxazolidin-5-yl)methyl]oxy}thiochroman is obtained.

Yield: 95% Melting point: 90° C.

EXAMPLE 46

8-{[(2-Oxooxazolidin-5-yl)methyl]oxy}thiochroman 17.22 g of N,N'-carbonyldiimidazole are added to 1.7 g (7.1 mmol) of 8-[(3-amino-2-hydroxypropyl)oxy]thiochroman obtained in Step B of Example 34, dissolved in 10 cm$^3$ of anhydrous tetrahydrofuran.

The mixture is heated under reflux, with stirring, for 2 hours and then cooled, and the solvent is evaporated off under reduced pressure.

The crude product is then purified by chromatography over a silica column (eluant: methylene chloride).

0.86 g of 8-{[(2-oxooxazolidin-5-yl)methyl]oxy}thiochroman is obtained.

Yield: 51% Melting point: 152°–153° C.

EXAMPLE 47

8-{{4-Oxo-4-[4-(2-Methoxyphenyl)piperazin-1-yl]butyl}oxy}thiochroman

Step A: Ethyl 4-[(Thiochroman-8-yl)oxy]butyrate

Under argon and with stirring, 1.5 g (9.02 mmol) of 8-thiochromanol are dissolved in 5 cm$^3$ of dimethylformamide (DMF). 3.74 g (27.06 mmol) of K$_2$CO$_3$ are added and then 1.94 g (9.92 mmol) of ethyl 4-bromobutyrate dissolved in 6 cm$^3$ of DMF are added dropwise. The mixture is heated at 60° C. for 5 hours. The DMF is evaporated off. The residue is taken up in H$_2$O. The product is extracted with CH$_2$Cl$_2$ and then dried over MgSO$_4$. Purification over a silica column (eluant: ether/petroleum ether 3:7) yields 2.48 g of the title compound (white solid).

Yield: 98% Melting point: 31° C.

Step B: 4-[(Thiochroman-8-yl)oxy]butyric acid

Under argon and with stirring, 2.25 g (8.02 mmol) of the compound obtained in Step A are dissolved in 30 cm$^3$ of methanol. 4.5 cm$^3$ of a 10% potassium hydroxide solution are added dropwise. After 2 hours at room temperature, the methanol is evaporated off. The residue is acidified very slowly with a 2N hydrochloric acid solution. The resulting precipitate is extracted with CH$_2$Cl$_2$ and dried over MgSO$_4$. 1.94 g of a white solid are recovered.

Yield: 96% Melting point: 115° C.

Step C:
8-{{4-Oxo-4-[4-(2-methoxyphenyl)piperazin-1-yl]butyl}oxy}thiochroman

Under argon and with stirring, 700 mg (2.77 mmol) of the acid obtained in the preceding step are dissolved in 5 cm$^3$ of DMF.

The mixture is cooled in ice. 590 mg (3.05 mmol) of 1-(3-dimethylaminopropyl)-3-ethylcarbodiimide and 425 mg (2.77 mmol) of 1-hydroxybenzotriazole hydrate are added, followed by 590 mg (3.05 mmol) of 1-(2-methoxyphenyl)piperazine dissolved in 5 cm$^3$ of DMF.

The mixture is allowed to come to room temperature. After 24 hours, the DMF is evaporated off. The residue is taken up in H$_2$O and then extracted with CH$_2$Cl$_2$. The product is dried over MgSO$_4$ and purified over a silica column (eluant: ether), yielding 1.12 g of a yellow oil (base).

Yield: 95% Melting point (fumarate): 235° C.

EXAMPLE 48

8-{{3-[4-(2-Methoxyphenyl)piperazin-1-yl]-3-oxopropyl}oxy}thiochroman

Under argon, 110 mg (4.61×10$^{-4}$ mol) of 3-[(thiochroman-8-yl)oxy]propionic acid (Indian Journal of Chemistry (1977) 15 pp. 715–719) are dissolved in 1.5 cm$^3$ of dimethylformamide. The flask is cooled in an ice-bath. 100 mg (5.07×10$^{-4}$ mol) of 1-(3-dimethylaminopropyl)-3-ethylcarbodiimide hydrochloride, 71 mg (4.61×10$^{-4}$ mol) of 1-hydroxybenzotriazole and 100 mg (5.07×10$^{-4}$ mol) of 1-(2-methoxyphenyl)piperazine are added. The mixture is allowed to come gradually to room temperature. After 24 hours, the solvent is evaporated off. The residue is taken up in H$_2$O and extracted with CH$_2$Cl$_2$. The product is dried over MgSO$_4$.

The product is purified over a silica column. Eluant: ethyl acetate: 100%. There are recovered 180 mg of the title compound (white solid), which is recrystallised from ethanol.

Yield: 95% Melting point: 100° C.

EXAMPLE 49

8-[(4-Phthalimidobutyl)oxy]thiochroman

Under argon and with stirring, 500 mg (3.01 mmol) of 8-thiochromanol and 930 mg (3.31 mmol) of N-(4-bromobutyl)phthalimide are dissolved in 4 cm$^3$ of dimethylformamide (DMF). 1.25 g (9.03 mmol) of K$_2$CO$_3$ are added. The mixture is heated at 60° C. for 6 hours. The DMF is evaporated off. The residue is taken up in H$_2$O. The product is extracted with CH$_2$Cl$_2$ and dried over MgSO$_4$. Purification over a silica column (eluant: CH$_2$Cl$_2$) yields 1.08 g of the title compound (white solid).

Yield: 98% Melting point: 116° C.

EXAMPLE 50

8-[(3-Phthalimidopropyl)oxy]thiochroman

Following the procedure of Example 49 but replacing N-(4-bromobutyl)phthalimide with N-(3-bromopropyl)phthalimide, the title compound is obtained.

Recrystallisation solvent: isopropanol Yield: 99% Melting point: 137° C.

EXAMPLE 51

8-[(2-Phthalimidoethyl)oxy]thiochroman

Following the procedure of Example 49 but replacing N-(4-bromobutyl)phthalimide with N-(2-bromoethyl)phthalimide, the title compound is obtained.
Melting point: 166° C.

EXAMPLE 52

8-{{3-[4-(2-Methoxyphenyl)piperazin-1-yl]-2-methyl-propyl}oxy}thiochroman

Step A: 8-[(3-Chloro-2-methylpropyl)oxy]thiochroman

Under argon, 5 g (30.08 mmol) of thiochromanol are dissolved in 40 cm$^3$ of dimethylformamide (DMF). 790 mg (33.08 mmol) of sodium hydride are added in small portions. After 30 minutes at 60° C., 12.89 g (75.19 mmol) of 1-bromo-3-chloro-2-methylpropane dissolved in 10 cm$^3$ of DMF are added. The mixture is heated at 60° C. for 24 hours.

The solvent is evaporated off and then the residue is extracted with methylene chloride, after hydrolysis. The crude product is dried over MgSO$_4$. After evaporation, the crude product is passed over a normal silica column (eluant: ether/petroleum ether 5:95). There are obtained 3.79 g of a colourless oil which contains the mixture of 8-[(3-chloro-2-methylpropyl)oxy]thiochroman and its bromine and ethylene analogues. That mixture is used without further purification in the following step.

Step B:
8-{{3-[4-(2-Methoxyphenyl)piperazin-1-yl]-2-methyl-propyl}oxy}thiochroman Under argon, 3.54 g of the mixture obtained in the preceding step are dissolved in 20 cm$^3$ of DMF. 2.67 g (20.68 mmol) of N,N-diisopropylethylamine, dissolved in 5 cm$^3$ of DMF, and 3.98 g (20.08 mmol) of 1-(2-methoxyphenyl)piperazine, dissolved in 5 cm$^3$ of DMF, are added. The mixture is heated at 80° C. for 24 hours. The solvent is evaporated off, and then water is added. The product is extracted with methylene chloride and dried over MgSO$_4$. After evaporation, the product is purified over a normal silica column (eluant: CH$_2$Cl$_2$: 100%, then CH$_2$Cl$_2$/ethyl acetate 2:1) in order to obtain the title compound.

Overall yield: 20% Melting point (fumarate): 189° C.

EXAMPLE 53

8-{[3-(4-Phenylpiperidin-1-yl)propyl]oxy}thiochroman

Under argon, 600 mg (2.09 mmol) of 8-[3-(bromopropyl)oxy]thiochroman are dissolved in 6 cm$^3$ of acetonitrile. N,N-diisopropylethylamine (405 mg; 3.13 mmol) dissolved in 5 cm$^3$ of acetonitrile is added, followed by 4-phenylpiperidine (505 mg; 3.13 mmol) dissolved in 5 cm$^3$ of acetonitrile. The mixture is refluxed for one night.

The acetonitrile is evaporated off. The reaction mixture is taken up in water and extracted with methylene chloride. The product is purified over a flash silica column. Eluant: methanol/CH$_2$Cl$_2$ 5:95. The title compound is obtained (orange-coloured solid).

Recrystallisation solvent: ethanol Overall yield: 85% Melting point: 78°–79° C.

EXAMPLES 54 TO 56

Following the procedure of Example 53, the compounds of the following Examples are obtained starting from the appropriate amine:

EXAMPLE 54

8-{[3-(4-Phenylpiperazin-1-yl)propyl]oxy}thiochroman

Crystallisation solvent: ethanol Yield: 85% Melting point: 102° C.

EXAMPLE 55

8-{{3-[4-(4-Fluorophenyl)piperazin-1-yl]propyl}oxy}thiochroman

Yield: 86% Melting point: 106@C.

EXAMPLE 56

8-{{3-[4-(Dicyclopropylmethyl)piperazin-1-yl]propyl}oxy}thiochroman

EXAMPLE 57

8-{{3-[(5-Methoxy-dihydro-[2H]-benzo[b]pyran-3-yl)amino]propyl}oxy}thiochroman Under argon, 1.6 g (5.58 mmol) of 8-[(3-bromopropyl)oxy]thiochroman, 1 g (5.58 mmol) of 3-amino-5-methoxy-dihydro-[2H]-benzo[b]pyran and 1.69 g (16.74 mmol) of triethylamine are dissolved in 20 cm$^3$ of dimethylformamide. The mixture is kept at room temperature for 24 hours. The solvent is evaporated off. The residue is taken up in H$_2$O and extracted with methylene chloride. The product is dried over MgSO$_4$. After evaporation, the product is purified over a flash silica column. Eluant: methanol/CH$_2$Cl$_2$ 5:95. The title compound is obtained (yellow oil).

Crystallisation solvent: acetone/ethanol Overall yield: 58% Melting point (fumarate): 156°–157° C.

EXAMPLE 58

8-{{4-[(5-Methoxy-dihydro-[2H]-benzo[b]pyran-3-yl)amino]butyl}oxy}thiochroman Following the procedure of Example 57 but starting from 8-[(4-bromobutyl)oxy]thiochroman (Step A, Example 2), the title compound is obtained.

Crystallisation solvent: ethanol/acetone Yield: 54% Melting point: 176°–177° C.

EXAMPLE 59

8-{[2-Hydroxy-3-(4-phenylpiperidin-1-yl)propyl]oxy}thiochroman

Following the procedure of Example 1 but using 4-phenylpiperidine in Step B, the title compound is obtained.

Yield: 97% Melting point: 104° C.

EXAMPLE 60

8-{[2-Methoxy-3-(4-phenylpiperidin-1-yl)propyl]oxy}thiochroman

Under argon, 100 mg (2.60×10$^{-4}$ mol) of the compound of Example 59 are dissolved in 2 cm$^3$ of tetrahydrofuran (THF). 10 mg (3.90×10$^{-4}$ mol) of sodium hydride are added. The mixture is stirred at room temperature for 15 minutes, and then 0.08 cm$^3$ (185 mg; 1.30 mmol) of iodomethane is added dropwise. The mixture is left at room temperature for one hour. The THF is evaporated off, and then the residue is gradually taken up in water. The mixture is extracted with methylene chloride. The product is dried over MgSO$_4$. The product is purified over a flash silica column. Eluant: ethylacetate:100%. The title compound is recovered (oil).

Yield: 82% Melting point (fumarate): 169° C.

EXAMPLES 61 TO 64

Following the procedure of Examples 59 and 60 but using the appropriate amine, the compounds of the following Examples are obtained:

EXAMPLE 61

8-{[2-Hydroxy-3-(4-phenylpiperazin-1-yl)propyl]oxy}thiochroman

Yield: 71% Melting point: 91° C.

EXAMPLE 62

8-{[2-Methoxy-3-(4-phenylpiperazin-1-yl)propyl]oxy}thiochroman

Crystallisation solvent: ethanol Yield: 79% Melting point: 86° C.

EXAMPLE 63

8-{{2-Hydroxy-3-[4-(dicyclopropylmethyl)piperazin-1-yl]propyl}oxy}thiochroman

EXAMPLE 64

8-{{2-Methoxy-3-[4-(dicyclopropylmethyl)piperazin-1-yl]propyl}oxy}thiochroman

EXAMPLES 65 TO 68

Following the procedure of Example 1 but using the appropriate amine in Step B, the compounds of the following Examples are obtained:

EXAMPLE 65

8-{{2-Hydroxy-3-[(4-phenylbutyl)amino]propyl}oxy}thiochroman

Crystallisation solvent: isopropanol Yield: 94% Melting point: 71° C.

EXAMPLE 66

8-{{2-Hydroxy-3-[(3-phenylpropyl)amino]propyl}oxy}thiochroman

Crystallisation solvent: ethanol Yield: 93% Melting point: 94° C.

EXAMPLE 67

8-{{3-[(Cyclooctyl)amino]-2-hydroxypropyl}oxy}thiochroman

Crystallisation solvent: ethanol Yield: 94% Melting point: 97° C.

EXAMPLE 68

8-{{3-[(Adamantyl)amino]-2-hydroxypropyl}oxy}thiochroman

Crystallisation solvent: cyclohexane Yield: 81% Melting point: 92° C.

EXAMPLE 69

8-{{2-[N,N-bis-(4-phthalimidobutyl)amino]ethyl}oxy}thiochroman

Step A: 2-[(Thiochroman-8-yl)oxy]ethylamine

Under argon, 2 g (12.03 mmol) of 8-thiochromanol are dissolved in 15 cm$^3$ of DMF. 5 g (36.09 mmol) of potassium carbonate and a catalytic amount of potassium iodide are added. Then 5.45 g (72.18 mmol) of chloroacetonitrile dissolved in 5 cm$^3$ of dimethylformamide (DMF) are added dropwise. The mixture is heated at 60° C. for 4 hours, and then the solvent is evaporated off. The residue is taken up in H$_2$O and extracted with methylene chloride and then dried over MgSO$_4$. After evaporation, the product is purified over a silica column. Eluant: methanol/CH$_2$Cl$_2$ 1:99. 2.44 g of 2-(thiochroman-8-yl-oxy)acetonitrile are obtained (melting point: 66° C.).

In a Woulfe bottle, under argon, 480 mg (12.67 mmol) of lithium aluminium hydride are suspended in 20 cm$^3$ of anhydrous ether. With the aid of a dropping funnel, 1 g (4.87 mmol) of the nitrile obtained above, dissolved in 20 cm$^3$ of anhydrous ether, is added dropwise. After 5 minutes at room temperature, the Woulfe bottle is placed in an ice-bath and hydrolysis is carried out slowly with pieces of ice until the aluminates precipitate. The ethereal phase is removed and then the salts are washed several times with ether. The ethereal phases are combined. They are dried over MgSO$_4$ and then the solvent is evaporated off while cold. There is obtained the title compound (colourless oil), which does not require purification.

Yield: 93%

Step B:
8-{{2-[N,N-bis-(4-phthalimidobutyl)amino]ethyl}oxy}thiochroman

Under argon, 200 mg (9.55×10$^{-4}$ mol) of the amine obtained in Step A, 670 mg (2.39 mmol) of N-(4-bromobutyl)phthalimide and 185 mg (1.43 mmol) of N,N-diisopropylethylamine are dissolved in 13 cm$^3$ of acetonitrile. The mixture is refluxed for 15 hours, and then the solvent is evaporated off. The residue is taken up in H$_2$O and extracted with methylene chloride. After evaporation, the product is purified over a silica column. Eluant: AcOEt/CH$_2$Cl$_2$ 1:1. There are obtained 340 mg of the title compound (oil), which precipitates in acetone.

Yield: 58% Melting point: 66° C.

EXAMPLE 70

8-{{2-[N-(4-phthalimidobutyl)amino]ethyl}oxy}thiochroman

Step A: 2-[(Thiochroman-8-yl)oxy]ethylamine

Step B:
8-{{2-[N-(4-phthalimidobutyl)amino]ethyl}oxy}thiochroman

Under argon, 1 g (4.78 mmol) of the amine of Step A, 1.35 g (4.78 mmol) of N-(4-bromobutyl)phthalimide and 2 cm$^3$ (1.45 g; 14.33 mmol) of triethylamine are dissolved in 20 cm$^3$ of dimethylformamide (DMF).

The mixture is kept at room temperature for 24 hours. The solvent is evaporated off. The residue is taken up in H$_2$O and extracted with methylene chloride. The product is dried over MgSO$_4$. After evaporation, the product is purified over a silica column. Eluant: ethylacetate/methanol 9:1. The title compound is obtained (brown solid).

Recrystallisation solvent: ethanol Yield: 60% Melting point: 175° C.

EXAMPLE 71

8-{{3-[N-(5-methoxy-dihydro-[2H]-benzo[b]pyran-3-yl-N-propylamino]propyl}oxy}thiochroman Melting point (fumarate): 79° C. Crystallisation solvent: cyclohexane

EXAMPLE 72

8-{{2-Methoxy-3-[(4-phenylbutyl)amino]propyl}oxy}thiochroman

Melting point (fumarate): 106° C. Crystallisation solvent: ethanol/acetone

PHARMACOLOGICAL STUDY OF THE COMPOUNDS OF THE INVENTION

Example A: Acute Toxicity Study

Acute toxicity was assessed following oral administration of increasing doses (0.1–0.25–0.50–0.75–1 g/kg$^{-1}$) of the products of the invention to groups of five mice (20±2 grams).

The animals were observed at regular intervals during the first day and daily during the two weeks following the treatment. It appears that the compounds of the invention are completely non-toxic. No death is observed after administration of a dose of 1 g/kg$^{-1}$. No problems are observed following administration of that dose.

Example B: Measurement of the Affinity of the Compounds of the Invention for 5-HT$_{1A}$ Receptprs

Protocol

The in vitro affinity of the compounds of the invention for 5-HT$_{1A}$ serotoninergic receptors was determined by measuring the displacement of (3H) 8-hydroxy-2-(N,N-dipropylamino)tetraline [or (3H) 8-OH-DPAT], a selective agonist of that receptor, on hippocampus preparations from rats.

Results

The compounds of the general formula (I) prove to be very powerful ligands of 5-HT$_{1A}$ receptors, with affinity constants of the order of the nanomolar.

Example C: Measurement of the Affinity of the Compounds of the Invention for $\beta_1$, $\beta_2$, D$_1$, D$_2$, 5-HT$_{1C}$, 5-HT$_{1D}$, 5-HT$_2$ and 5-HT$_3$ Receptors

Protocol

The in vitro affinity of the compounds of the invention was determined:

for $\beta_1$ adrenergic receptors, by measuring the displacement of dihydroalprenolol, on frontal cortex preparations from rats, for $\beta_2$ adrenergic receptors, by measuring the displacement of dihydroalprenolol, on pulmonary parenchyma preparations from rats, for D$_1$ dopaminergic receptors, by measuring the displacement of SCH 23390, on striatum preparations from rats, for D$_2$ dopaminergic receptors, by measuring the displacement of Raclopride, on striatum preparations from rats, for 5-HT$_{1C}$ serotoninergic receptors, by measuring the displacement of N-methylmesulergine, on frontal cortex and hippocampus preparations from rats, for 5-HT$_{1D}$ serotoninergic receptors, by measuring the displacement of 5-OH-tryptamine, on cortex, striatum and globus pallidus preparations from rats, for 5-HT$_2$ serotoninergic receptors, by measuring the displacement of amino-iodo-ketaneserine, on frontal cortex preparations from rats, for 5-HT$_3$ serotoninergic receptors, by measuring the displacement of BRL 43694, on area postrema preparations from rats.

Results

Certain compounds of the invention have an affinity for $\beta_1$, $\beta_2$, D$_1$, D$_2$, 5-HT$_{1C}$, 5-HT$_{1D}$, 5-HT$_2$ and 5-HT$_3$ receptors that is considerably weaker than that for 5-HT$_{1A}$ receptors. The compounds of the invention are therefore selective ligands of 5-HT$_{1A}$ receptors.

Example D: Evaluation of the Antagonistic Activity of the Compounds of the Invention Towards 5-HT$_{1A}$ Receptors

Protocol

The antagonistic activity of the compounds of the invention towards 5-HT$_{1A}$ receptors was evaluated by stimulating adenylate cyclase, in the presence of the test compound, by 10 $\mu$M of forskolin, in the absence or in the presence of 0.1 $\mu$M of [8-hydroxy-2-(di-n-propylamino)tetraline] (8-OH-DPAT).

The products of the invention were tested for concentration ranges of from 10 nM to 10 $\mu$M.

Results

The compounds of the invention oppose in a competitive manner (IC$_{50}$<50 nM) the inhibition of adenylate cyclase, provoked by 8-OH-DPAT (0.1 $\mu$M), in rat hippocampus homogenates, which reflects a powerful antagonistic activity towards 5-HT$_{1A}$ receptors.

Example E: Study of the Anti-depressant Activity of the Compounds of the Invention

Principle

The products are studied using the "learned renouncement" model, which consists in inducing in the animal, by means of a series of uncontrollable adverse events, a deficit during subsequent avoidance tasks.

Protocol

Male Wistar rats weighing from 180 to 200 grams are used. The animals are kept in the animal house for one week prior to the test, in plastics boxes, in groups of 10, at an ambient temperature of 21° C.±1° C., with free access to water and food.

The animals are then isolated in small-sized boxes and are subjected to 60 unavoidable electric shocks (0.8 mA every minute±15 seconds). A group of control rats does not receive electric shocks.

The ability of the animals to learn avoidance (passing from one compartment to another in order to avoid the electric shocks) is assessed 48 hours later and for 3 consecutive days. During the learning sessions, the animals undergo two tests per minute for a period of 15 minutes. The number of avoidance failures is noted for each rat. The animals are treated (i.p.; 0.5 cm$^3$/100 g) 6 hours after the unavoidable shocks and 4 days thereafter, in the mornings 30 minutes before the learning session and in the evenings between 18.00 and 19.00.

The test products are dissolved in distilled water. The test products are administered at doses of 0.25 mg/kg/day.

Results

The test shows that the products of the invention significantly reduce the number of avoidance failures, which represents, for the products of the invention, a strong activity of the anti-depressant type.

Example F: Study of Anxiolytic Activity—So-Called Light/Dark Cage Test in Mice

Principle

It is proposed to study the anxiolytic effects of the compounds of the invention using the so-called light-/dark cage test in mice.

Protocol

This test was developed by Crawley et al. (1981, Pharmacol. Biochem. Behav.) and then modified and validated behaviourally.

Two PVC cages of equal size (20×20×14 cm) are used. One is brightly illuminated by a 100 W lamp ("cold" light) and the other is darkened. The two cages are separated by means of a small opaque tunnel (5×7 cm). The mice are introduced individually into the illuminated cage and, as soon as they have entered the dark cage for the first time, the time spent by the animals in the illuminated cage and the number of times they pass between the dark cage and the illuminated cage are recorded for a period of 5 minutes by means of keys connected to a computer.

Each test group comprises a minimum of 15 animals.

Results

The i.p. administration of certain products of the invention brings about a simultaneous increase in the time spent by the mice in the illuminated cage and in the number of times they pass between the dark cage and the illuminated cage.

That significant increase in the two parameters studied shows the remarkable anxiolytic activity of certain compounds of the invention.

Example G: Pharmaceutical Composition

Tablets containing 5 mg of 8-{{3-[4-(2-methoxyphenyl)piperazin-1-yl]-2-hydroxypropyl}oxy}thiochroman Formulation for 10,000 tablets:
- 8-{{3-[4-(2-methoxyphenyl)piperazin-1-yl]-2-hydroxypropyl}oxy}thiochroman ... 50 g
- wheat starch ... 75 g
- corn starch ... 75 g
- lactose ... 325 g
- magnesium stearate ... 10 g
- silica ... 5 g
- hydroxypropylcellulose ... 10 g

We claim:

1. A compound selected from those of formula (I):

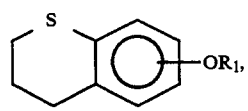

in which:
R₁ represents:

or a group of formula (B):

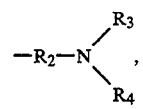

in which
$R_2$ is a group selected from:
—R′₂—, wherein R′₂ represents a group —(CH₂)$_n$— or

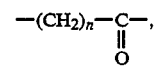

wherein n is 1 to 6, inclusive R′₂ being unsubstituted or substituted in the alkylene moiety by lower alkyl, aryl or aryl-lower alkyl, and

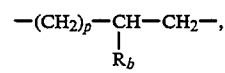

wherein p is 1, 2 or 3 and $R_b$ represents a radical selected from hydroxy, lower alkoxy, lower alkylcarbonyloxy, aryloxy, and aryl-lower alkoxy, one of $R_3$ and $R_4$, which are identical or different, each independently of the other represents a radical selected from:
hydrogen, and
lower alkyl unsubstituted or substituted by one or more radicals selected from halogen, hydroxy, and lower alkoxy, the other of $R_3$ and $R_4$ being benzopyranyl, unsubstituted or substituted by one or more radicals selected from halogen, hydroxy, lower alkyl, lower alkoxy, and trifluoromethyl, wherein, unless indicated otherwise:
the term "aryl" means a phenyl or naphthyl group,
and the terms "lower alkyl" and "lower alkoxy" indicate linear or branched groups containing 1 to 6 carbon atoms inclusive, an optical isomer, in pure form or in the form of a mixture, and an addition salt thereof with a pharmaceutically-acceptable acid or base.

2. A compound according to claim 1 selected from those in which $R_2$ represents a group

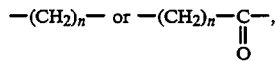

wherein n represents an integer of 1 to 6 inclusive, it being possible for the groups

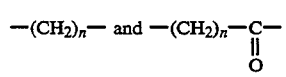

to be substituted in their alkylene moiety by lower alkyl, aryl, or aryl-lower alkyl, an optical isomer, in pure form or in the form of a mixture, and an addition salt thereof with a pharmaceutically-acceptable acid or base.

3. A compounds according to claim 1 selected from those in which $R_2$ represents a group

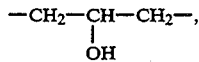

an optical isomer, in pure form or in the form of a mixture, and an addition salt thereof with a pharmaceutically-acceptable acid or base.

4. A compound according to claim 1 which is selected from 8-{{3-[(5-methoxy-dihydro-[2H]-benzo[b]-pyran-3-yl)amino]propyl}oxy}thiochroman, and an addition salt thereof with a pharmaceutically-acceptable acid.

5. A compound according to claim 1 which is 8-{{4-[(5-methoxydihydro-[2H]-benzo[b]pyran-3-yl)amino]-butyl}oxy}thiochroman.

6. A compound according to claim 1 which is selected from 8-{{3-[N-(5-methoxy-dihydro-[2H]-benzo[b]pyran-3-yl)-N-propylamino]propyl}oxy}thiochroman, and an addition salt thereof with a pharmaceutically-acceptable acid.

7. A pharmaceutical composition containing as active ingredient a compound according to claim 1, in combination with one or more pharmaceutically-acceptable excipients or carriers.

8. A method of treating a mammal afflicted with a disorder selected from stress, anxiety, depression, psychoses and, schizophrenia, comprising the step of administering to the said mammal an amount of a compound as claimed in claim 1 which is effective for alleviation of said disorder.

9. A method of treating a mammal afflicted with depression comprising the step of administering to the said mammal an amount of a compound as claimed in claim 1 which is effective for alleviation of said disorder.

* * * * *

UNITED STATES PATENT AND TRADEMARK OFFICE
CERTIFICATE OF CORRECTION

PATENT NO. : 5,371,103

DATED : December 6, 1994

INVENTOR(S) : Gèrald Guillaumet, Gèrard Cuodert, Tchao Podona, Bèatrice Guardiola-Lemaitre, Pierre Renard, Gèrard Adam, Daniel Henri-Caignard It is certified that error appears in the above-indentified patent and that said Letters Patent is hereby corrected as shown below:

Column 2, line 22; delete "-($CH_2$-"at the end of the line.
Column 2, line 23; insert "-($CH_2$" at the beginning of the line, before ")$_n$"
Column 13, line 52; insert ")" at the end of the line.
Column 13, line 53; delete the ")" at the beginning of the line.
Column 13, line 60; "(3-trifi-" should read -- (3-trifl- --
Column 13, line 64; delete "C-" at the end of the line.
Column 13, line 65; insert "C" at the beginning of the line.
Column 14, line 21; delete "butyl-" at the end of the line.
Column 14, line 22; insert "butyl" at the beginning of the line, before "]".
Column 14, line 26; "flucrophenyl)" should read
    -- fluorophenyl) --
Column 16, line 26; insert "]" at the end of the line before the hyphen.
Column 16, line 27; delete "]" at the beginning of the line.
Column 17, line 59; insert "]" at the end of the line before the hyphen.
Column 17, line 60; delete "]" at the beginning of the line.
Column 18, line 25; "(6,721" should read -- (6.721 --
Column 18, line 45; insert ")" at the end of the line before the hyphen.
Column 18, line 46; delete ")" at the beginning of the line.
Column 18, line 65; insert ")" at the end of the line before the hyphen.
Column 18, line 66; delete ")"at the beginning of the line.
Column 19, line 36; "methylio-" should read -- methyl io- --

UNITED STATES PATENT AND TRADEMARK OFFICE
CERTIFICATE OF CORRECTION

PATENT NO.  : 5,371,103

DATED       : December 6, 1994

INVENTOR(S) : Gèrald Guillaumet, Gèrard Coudert, Tchao Podona, Bèatrice Guardiola-Lemaitre, Pierre Renard, Gèrard Adam, Daniel Henri-Caignard It is certified that error appears in the above-indentified patent and that said Letters Patent is hereby corrected as shown below:

Column 20, line 15; "methyliodide" should read
   -- methyl iodide --
Column 21, line 16; insert "]" at the end of the line before the hyphen.
Column 21, line 17; delete "]" at the beginning of the line.
Column 24, line 19; insert "}" at the end of the line before the hyphen.
Column 24, line 20; delete "}" at the beginning of the line.
Column 25, line  4; "ethylacetate" should read
   -- ethyl acetate --
Column 26, line 65; "ethylacetate" should read
   -- ethyl acetate --
Column 30, line  1; delete the word "or"

Column 30, line 10; delete "-(CH$_2$-" at the end of the line.
Column 30, line 11; insert "-CH$_2$" at the beginning of the line before ")$_n$-"

Signed and Sealed this

Second Day of May, 1995

BRUCE LEHMAN

*Attest:*

*Attesting Officer*   Commissioner of Patents and Trademarks